(12) United States Patent
Derr (10) Patent No.: US 7,755,345 B2
(45) Date of Patent: Jul. 13, 2010

(54) MEASURING DEVICE WITH A PLUNGE-IN ELECTRODE

(75) Inventor: Andreas Derr, Wutöschingen-Degernau (DE)

(73) Assignee: Testo AG, Lenzkirch (DE)

( * ) Notice: Subject to any disclaimer, the term of this patent is extended or adjusted under 35 U.S.C. 154(b) by 0 days.

(21) Appl. No.: 10/182,857

(22) PCT Filed: Jan. 30, 2001

(86) PCT No.: PCT/EP01/00952

§ 371 (c)(1),
(2), (4) Date: Oct. 21, 2002

(87) PCT Pub. No.: WO01/57507

PCT Pub. Date: Aug. 9, 2001

(65) Prior Publication Data

US 2003/0057952 A1    Mar. 27, 2003

(30) Foreign Application Priority Data

Feb. 2, 2000   (DE) ................. 100 04 583

(51) Int. Cl.
*G01R 31/02*    (2006.01)
*G01K 1/00*    (2006.01)
(52) U.S. Cl. ................... 324/72.5; 374/208
(58) Field of Classification Search ........... 324/438, 324/754, 757, 690
See application file for complete search history.

(56) References Cited

U.S. PATENT DOCUMENTS

| | | | |
|---|---|---|---|
| 1,405,709 A * | 2/1922 | Black ................ 206/216 |
| 3,888,237 A | 6/1975 | Mori | |
| 3,989,038 A | 11/1976 | Neward | |
| 4,056,238 A * | 11/1977 | Ciniglio et al. ......... 242/472.6 |
| 4,218,299 A | 8/1980 | Lindell et al. ............. 204/435 |
| 4,252,124 A | 2/1981 | Maurer et al. ............. 600/361 |
| 4,312,734 A | 1/1982 | Nichols ................ 204/420 |
| 4,350,164 A | 9/1982 | Allain, Jr. | |
| 4,783,250 A | 11/1988 | Pons et al. .............. 204/400 |
| 4,901,446 A | 2/1990 | Narishige | |
| 4,959,130 A | 9/1990 | Josowicz et al. .......... 205/210 |
| 4,988,065 A * | 1/1991 | Leban et al. ............ 248/181.1 |
| 5,013,161 A * | 5/1991 | Zaragoza et al. .......... 374/208 |
| 5,279,168 A * | 1/1994 | Timm .................. 73/866.5 |
| 5,294,325 A | 3/1994 | Liu | |
| 5,354,449 A | 10/1994 | Band et al. .............. 204/443 |
| 6,086,584 A * | 7/2000 | Miller .................. 606/41 |
| 6,129,673 A * | 10/2000 | Fraden ................. 600/474 |
| 6,379,910 B1 * | 4/2002 | Nakamura et al. ......... 435/12 |
| 6,406,182 B1 * | 6/2002 | Chen .................. 374/208 |

FOREIGN PATENT DOCUMENTS

| | | |
|---|---|---|
| DE | 3814634 A1 | 4/1988 |
| DE | 3816458 A1 | 5/1988 |
| DE | 3825913 C1 | 8/1989 |
| DE | 3814634 A1 | 11/1989 |
| DE | 4105222 A1 | 2/1991 |

\* cited by examiner

*Primary Examiner*—Jeff Natalini
(74) *Attorney, Agent, or Firm*—Muirhead and Saturnelli, LLC (57) ABSTRACT

Described is a measuring device, in particular for measuring the pH value in foodstuffs. The measuring device comprises an extended first electrode for plunging into a material to be measured and a sheath which at least partially surrounds the first electrode. The first electrode is pivotably mounted in order to prevent breakage as a result of transversal loads exerted perpendicularly to the axial direction of the electrode.

40 Claims, 5 Drawing Sheets

MEASURING DEVICE WITH A PLUNGE-IN ELECTRODE

BACKGROUND

1. Technical Field

The present invention relates to a measuring device having an extended first electrode for being inserted into a material to be measured and having a sheath which at least partially surrounds the first electrode.

2. Description of Related Art

Such measuring devices are used, for example, for measuring the pH of foodstuffs such as meat, for example. Typically, a chamber is formed between the first electrode and the sheath in which a second electrode formed from a gel, for example, is installed. Both electrodes are connected to an evaluation circuit to determine the pH of a liquid of the material to be measured which has infiltrated between the electrodes.

For the measurement, the measuring device having the first electrode is pushed with great force into the material to be measured, resulting in a considerable mechanical load on the first electrode. First electrodes for pH measurement are usually made of glass, or have glass as the sheath, and can bear a high load in the axial direction and thus in the insertion direction. Perpendicular to the axial direction, these first electrodes are capable of bearing only a light load due to the brittleness of glass, which can result in breakage when a load is applied in this direction, as when the measuring device is tilted during insertion or withdrawal.

To avoid this problem, measuring devices have been provided in which the glass electrode or the gel surrounding the glass electrode is enclosed by a glass sheath and then by a metal or plastic sleeve. Although the load-bearing capacity of the glass electrode perpendicular to the axial direction does increase somewhat, the slightest deformations of the sheath, which are transmitted directly to the glass electrode, result in breakage of the first electrode and/or the glass sleeve surrounding the gel.

The double sheath made of glass and plastic also results in a larger diameter in the region of the probe tip, which during measurement creates large holes in the material to be measured.

It may be desirable to provide a measuring device having a first electrode which is more robust with respect to loads applied perpendicularly to the axial direction.

SUMMARY OF THE INVENTION

According to one aspect of the present invention, the extended first electrode for the measuring device is pivotably mounted so that when subjected to a load that is perpendicular to the axis, the first electrode is able to resist this load to a certain degree, thereby avoiding breakage of the first electrode, which preferably is designed as a glass electrode.

In order for the first electrode to be able to pivot under a transverse load, it is necessary for the sheath to also follow a pivoting motion of the first electrode, in a direction perpendicular to the electrode axis. For this purpose, the sheath preferably is made of a flexible, non-brittle material such as a flexible plastic. According to one embodiment of the present invention, the bending characteristics of the sheath are improved by increasing a diameter of the sheath in the region of the holding fixture, or in the region of an "imaginary hinge point," for the glass electrode. The imaginary hinge point is a point on the first electrode about which the first electrode is able to pivot as the result of an articulated support in the holding fixture, this point not changing its position when the first electrode pivots. In the first electrode according to the present invention, glass sheathing around the gel forming the second electrode is not required for stabilization.

The pivotable mounting for the first electrode is preferably created by a holding fixture which accommodates the first electrode at one end. To this end, the holding fixture preferably has a recess which accommodates the first electrode, a base region of the recess forming a support for one axial end of the first electrode. According to one embodiment of the present invention, lateral support for the first electrode is provided by arranging a ring-shaped element surrounding the first electrode between the first electrode and a side face of the recess. The ring-shaped element, which preferably is made of a flexible material such as an elastomer, in particular silicone, supports the glass electrode, at its end which is introduced into the recess, against the side faces of the recess in order to hold the first electrode essentially parallel to the side faces in a resting position when a transverse load is not present. Under a transverse load, the flexible ring-shaped element enables the first electrode to laterally pivot in order to avoid breakage of the first electrode.

According to one embodiment of the present invention, the ring-shaped element has an essentially circular cross-section similar to that of an O-ring, which surrounds the first electrode in the region of the opening in the recess and supports the first electrode against the side face. Below the ring and between the first electrode and the side face of the recess an air gap is formed which allows the end of the glass electrode to move sideways.

According to a further embodiment of the present invention, the ring-shaped element essentially has the design of a sleeve which partially or totally encloses the first electrode at the end section which is introduced into the recess. An elastic deformation of the sleeve allows the first electrode to pivot under a stress which is perpendicular to the axis.

According to a further embodiment of the present invention, a recess is provided with an essentially truncated cone-shaped design, a lower end of the recess having the smallest diameter and forming a support for an axial end of the first electrode. In this embodiment, lateral support of the first electrode is not provided in the recess. Due to the conical shape of the receptacle, the first electrode becomes "centered" in the initial position after the transverse load is removed. The lateral stability is essentially provided by the sheath, which surrounds the first electrode in at least one location. Lateral pivoting motions of the first electrode at the end which is introduced in the recess are made possible by the upwardly increasing diameter of the recess.

According to a further embodiment of the present invention, the first electrode is mounted using a ball-and-socket joint, the first electrode preferably being glued in place in a receptacle in one of the two joint halves.

In addition, according to another aspect of the present invention the first electrode is secured in a receptacle in a flexible shank, preferably by gluing.

BRIEF DESCRIPTION OF THE DRAWINGS

The present invention is explained in more detail hereinafter in exemplary embodiments, with reference to the figures.

DESCRIPTION OF EMBODIMENT(S)

Unless indicated otherwise, identical reference numbers in the figures denote identical parts having the same meaning.

Figure 1:
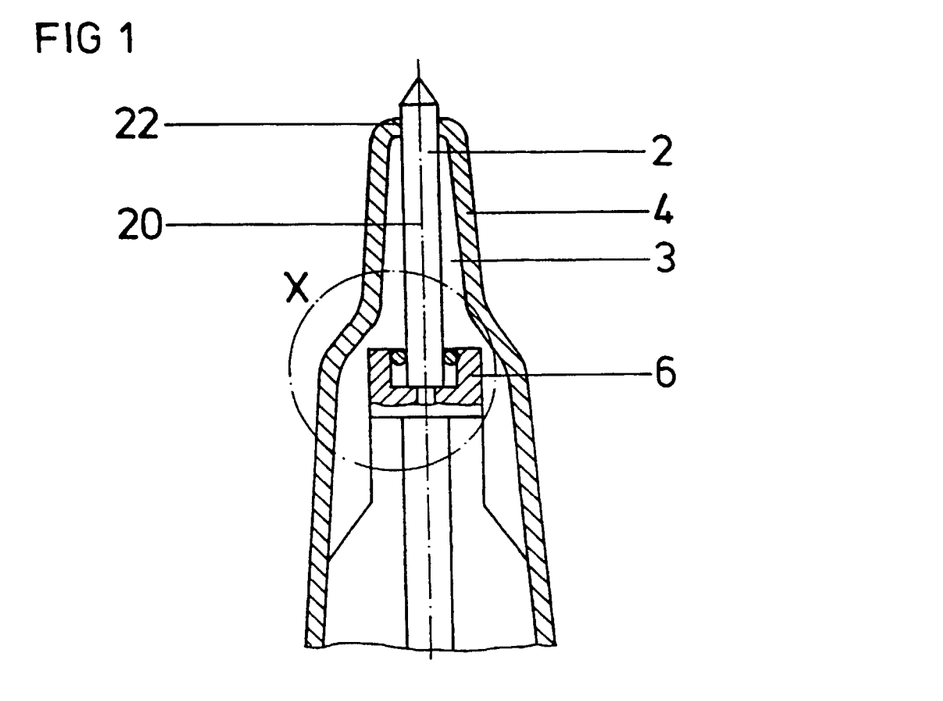
FIG. 1 shows a detail of a measuring device according to the present invention, in a cross-sectional side view.

FIG. 1 shows a detail of a measuring device according to the present invention in a cross-sectional side view. The measuring device has an extended, essentially cylindrical first electrode 2 and a sheath 4 which at least partially surrounds first electrode 2. First electrode 2 is preferably made of glass, or has a sheath made of glass, and is used as the electrode for the measuring device during the determination of the pH in a material to be measured. In the exemplary embodiment, a chamber is formed between first electrode 2 and sheath 4 in which a second electrode 3, preferably designed as a gel, is situated.

Figure 8:
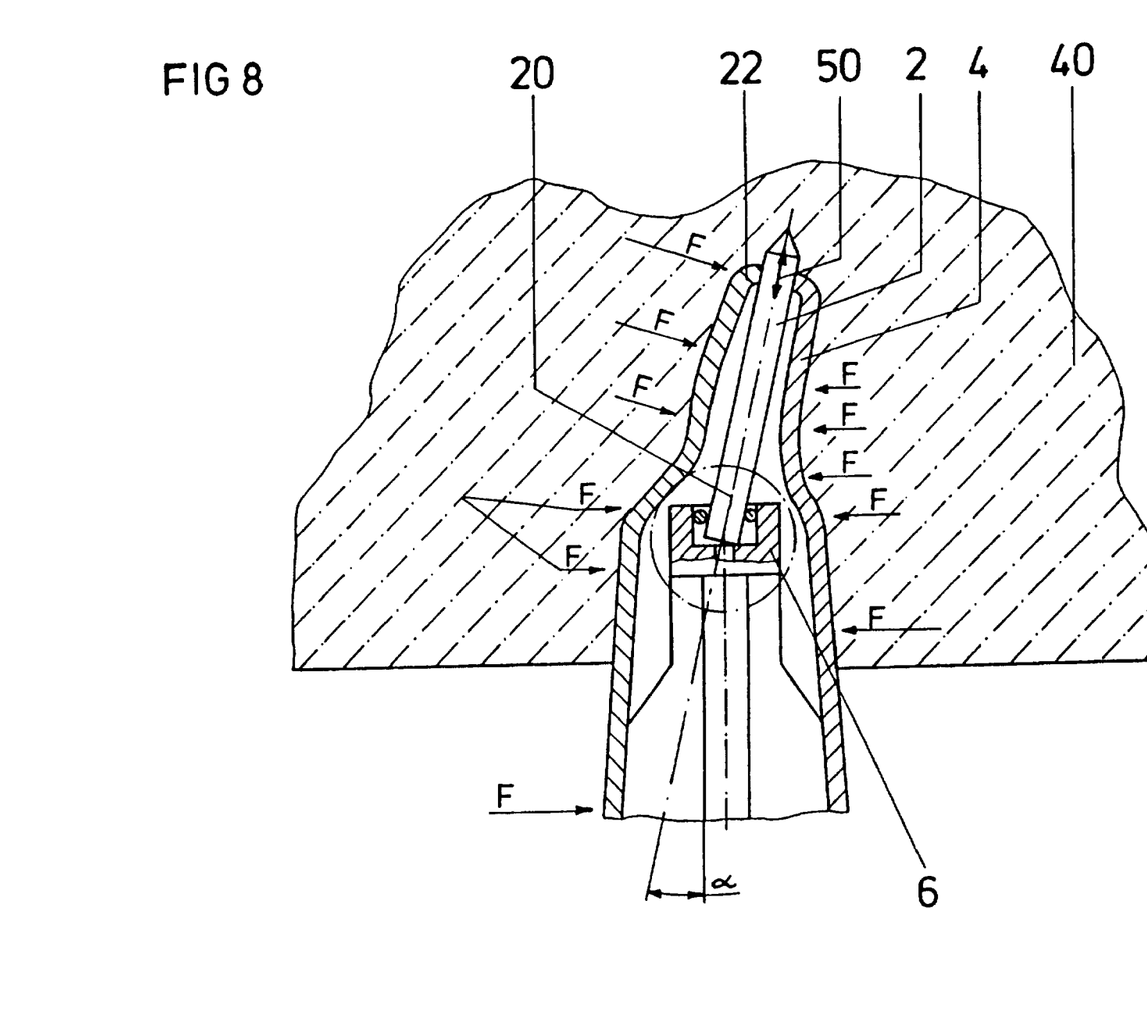
FIG. 8 shows a detail of a measuring device according to the present invention during measurement under a load exerted by lateral forces.

For the measurement, the front region of the measuring device is inserted into the material to be measured, which is usually a foodstuff, as illustrated by example in FIG. 8, liquid from the material to be measured reaching the area between first electrode 2 and second electrode 3 via appropriate measures (not illustrated in greater detail here) such as a diaphragm, for example. First electrode 2 has an insertion tip on a front end to facilitate insertion into the material to be measured.

A section of the measuring device, not illustrated in greater detail, has processing and display devices which are not explained in more detail here and which therefore are not illustrated. Both electrodes 2, 3 have an electrical connection to the processing device for the determination and display of the measured value.

According to the embodiment illustrated in FIG. 1, first electrode 2 is pivotably mounted. To this end, a holding fixture 6 is provided in the region of an end 10 of first electrode 2 facing away from the probe tip. Sheath 4 is made of a flexible material which allows first electrode 2 to pivot. A detailed illustration of the holding fixture according to FIG. 1 is shown in FIG. 2.

Insertion electrodes made of glass are well capable of bearing a load in the axial direction, but break easily under transverse loads, i.e., under loads applied perpendicular to the axial direction. The pivotable mounting, using holding fixture 6 at end 10 and flexible sheath 4, enables first electrode 2 to resist transverse loads resulting from tilting of the measuring device during insertion into the material to be measured or during withdrawal from the material to be measured, for example. The pivotable mounting does not increase the lateral stability of first electrode 2, but, rather, only allows first electrode for the measuring device according to the present invention to pivot under transverse loads.

Holding fixture 6 has a recess 8 in which the end section of first electrode 2 is accommodated, a base region 16 of recess 8 forming a support for axial end 10 of first electrode 2 in order to support the probe against axial forces F. In the exemplary embodiment, base 16 of recess 8 has an opening 18 for the passage of connection leads, the diameter of opening 18 being smaller than the diameter of probe 2. The connection lead may also be supplied to first electrode 2 in a groove on the side of the recess or in another suitable manner.

Figure 2A:
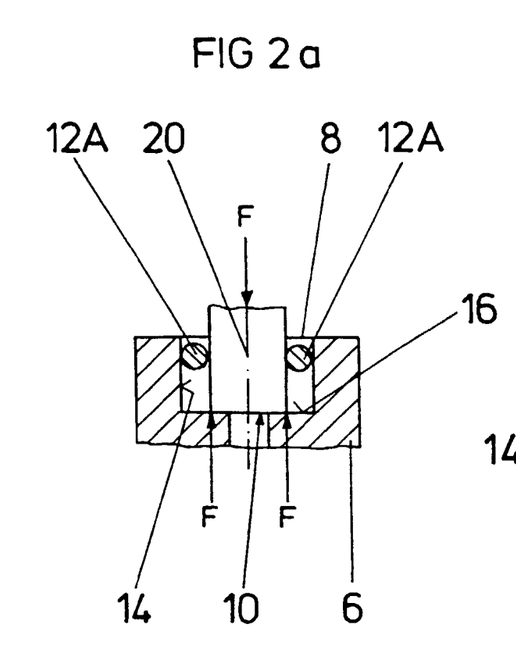
FIG. 2a shows a detailed illustration of a holding fixture for accommodating the first electrode according to a first embodiment, with the first electrode in the unswiveled position.
Figure 2B:
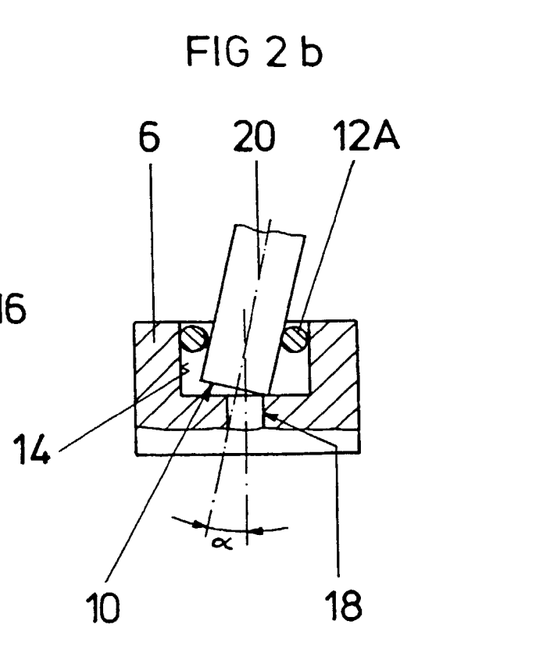
FIG. 2b shows a detailed illustration of a holding fixture for accommodating the first electrode according to a first embodiment, with the first electrode in the swiveled position.

In the exemplary embodiment according to FIG. 2, first electrode 2 is supported against side face 14 of recess 8 by a ring-shaped element 12A which is designed in the form of an O-ring. Ring 12A is preferably made of an elastomer such as silicone, NBR, or the like. Ring 12A supports the first electrode in the region just under the opening in recess 8. An air gap is formed below ring 12A, between first electrode 2 and side face 14, which allows end 10 of probe 2 situated below ring 12A to move sideways under a transverse load on probe 2, as illustrated in FIG. 2b. Probe 2 pivots about an imaginary hinge point 20, which in the illustrated example is a point on the axis of first electrode 2 which maintains its position when first electrode 2 is pivoted. When ring 12A and sheath 4 have good elasticity, the pivoting motion of the probe ends when probe 2 makes contact with two points on side face 14 or on the upper edge of recess 8. The elasticity of ring 12A and of sheath 4 are preferably matched to one another in such a way that, in order to avoid the danger of breakage, first electrode 2 is not able to pivot until it reaches the edge of recess 8, and that the pivoting range of the first electrode is determined solely or at least substantially by the design of sheath 4.

First electrode 2 is closely surrounded by sheath 4 in at least one location 22 on sheath 4, with the result that sheath 4 guides first electrode 2 and assists with the pivotable mounting of the first electrode. In order for first electrode 2 to make a pivoting motion, sheath 4 is preferably made of a flexible material such as plastic. Ideally, an imaginary hinge point of sheath 4 coincides with imaginary hinge point 20 of first electrode 2. The hinge point of sheath 4 may be determined by the geometry of the sheath. In the embodiment illustrated in FIG. 1, the inner and outer diameter of sheath 4 increases in the region of holding fixture 6 or in the region of imaginary hinge point 20 of first electrode 2. To this end, sheath 4 preferably has a truncated cone-shaped design in this region.

Figure 3A:
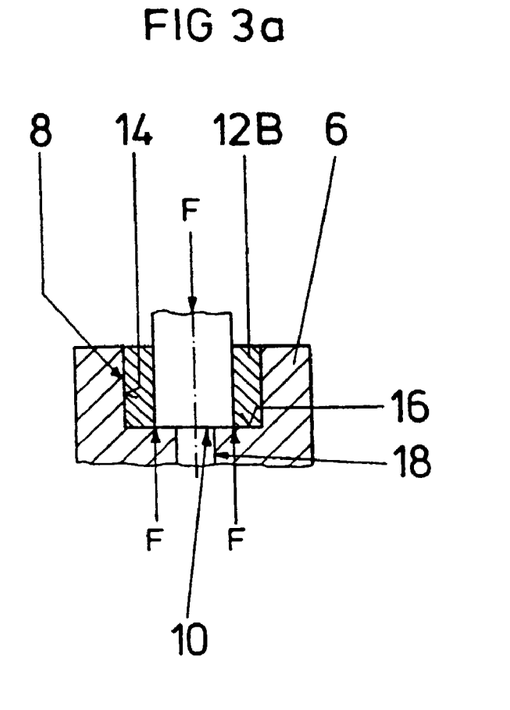
FIG. 3a shows a detailed illustration of a holding fixture for accommodating the first electrode according to a second embodiment, with the first electrode in the unswiveled position.
Figure 3B:
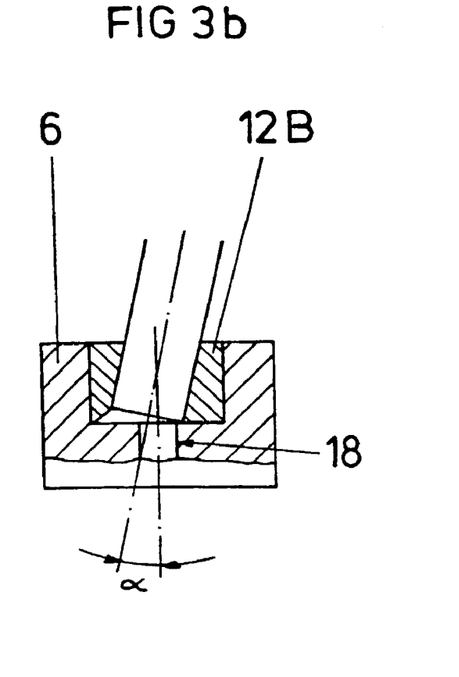
FIG. 3b shows a detailed illustration of a holding fixture for accommodating the first electrode according to a second embodiment, with the first electrode in the swiveled position.

FIG. 3 shows a further exemplary embodiment of a holding fixture 6 for the pivotable mounting of first electrode 2. Holding fixture 6 has a recess 8 in which an end section of probe 2 is accommodated, base 16 of recess 8 forming a support against axial forces F. A ring-shaped element 12B having a sleeve-like design which surrounds probe 2 in the region of the end section is provided for lateral support, and is introduced between probe 2 and side face 14 of recess 8. Sleeve 12B is formed from a flexible material, preferably an elastomer, which under a transverse load on first electrode 2 is elastically deformed to enable first electrode 2 to pivot, as illustrated in FIG. 3b.

The elasticity of sheath 4, which is essential for pivoting of first electrode 2, is matched to the transverse load-bearing capacity of first electrode 2. Thus, to ensure easy handling, sheath 4 should not be so elastic that probe 2 yields to the side, even under small transverse loads for which there is no danger that probe 2 may break, thereby making it more difficult to introduce the probe into the material to be measured.

Figure 4A:
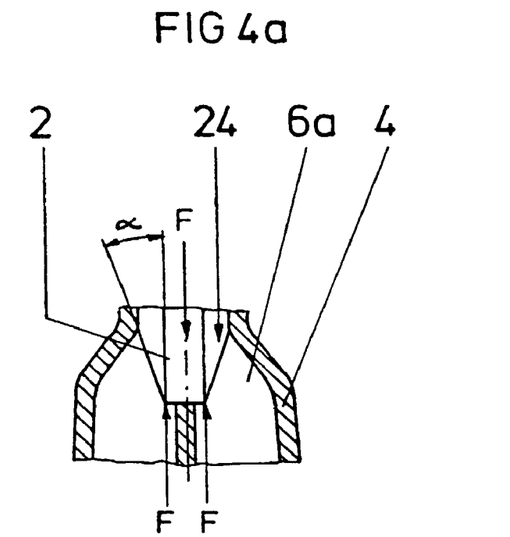
FIG. 4a shows a detailed illustration of a holding fixture for accommodating the first electrode according to a third embodiment, with the first electrode in the unswiveled position.
Figure 4B:
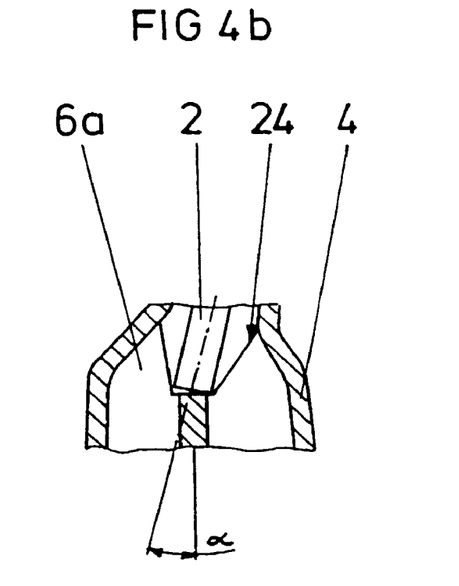
FIG. 4b shows a detailed illustration of a holding fixture for accommodating the first electrode according to a third embodiment, with the first electrode in the swiveled position.

A further embodiment of a holding fixture 6 is illustrated in FIG. 4. Holding fixture 6a has a truncated cone-shaped recess 24 whose lower end, which has the smallest diameter, forms a support for probe 2 against axial forces F. In this embodiment, holding fixture 6A does not provide lateral support for probe 2. Due to the conical shape of recess 24, the first electrode becomes "centered" in the initial position after the transverse load is removed. In this embodiment, lateral stability is ensured by sheath 4 which surrounds probe 2 at point 22 according to FIG. 1. Truncated cone-shaped recess 24 allows probe 2 to pivot under a transverse load on the probe. Sheath 4 which holds the first electrode is part of the support for the insertion electrode. To prevent probe 2 from slipping on the base of recess 24, the smallest diameter of recess 24 at the base of recess 24 is preferably equal to or slightly larger than the diameter of first electrode 2. Recess 24 may have geometric shapes other than a truncated cone, in particular a cylinder, as in FIGS. 2 and 3, precautions being taken as appropriate against slippage of the axial end of the probe on the base of the recess. In these cases as well, lateral stability may be ensured by sheath 4, ring-shaped elements being omitted.

Figure 5A:
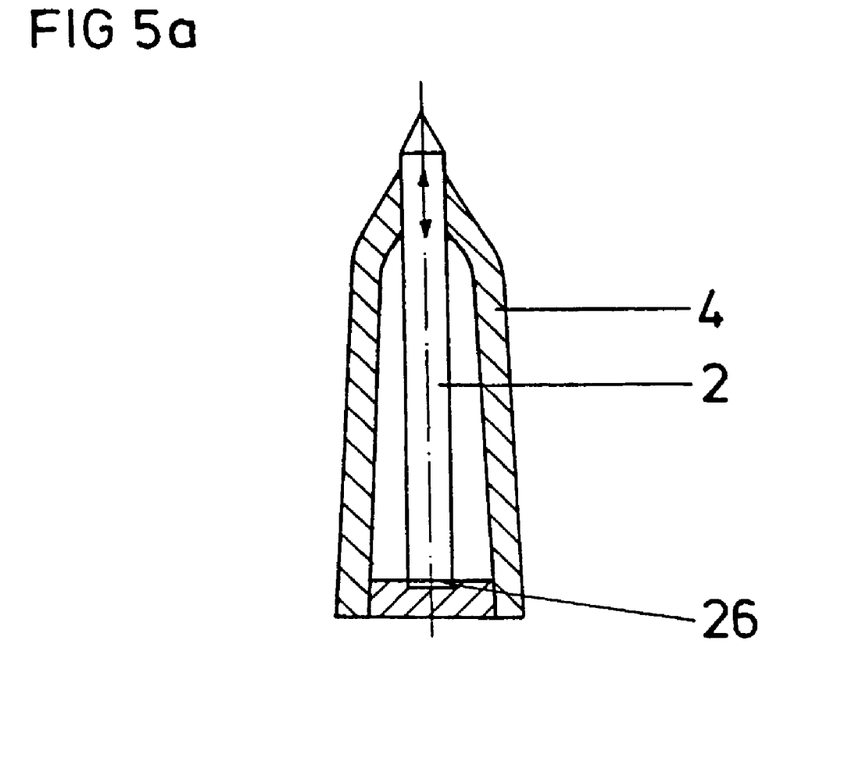
FIG. 5a shows a detailed illustration of a holding fixture for accommodating the first electrode according to a fourth embodiment, with the first electrode in the unswiveled position.
Figure 5B:
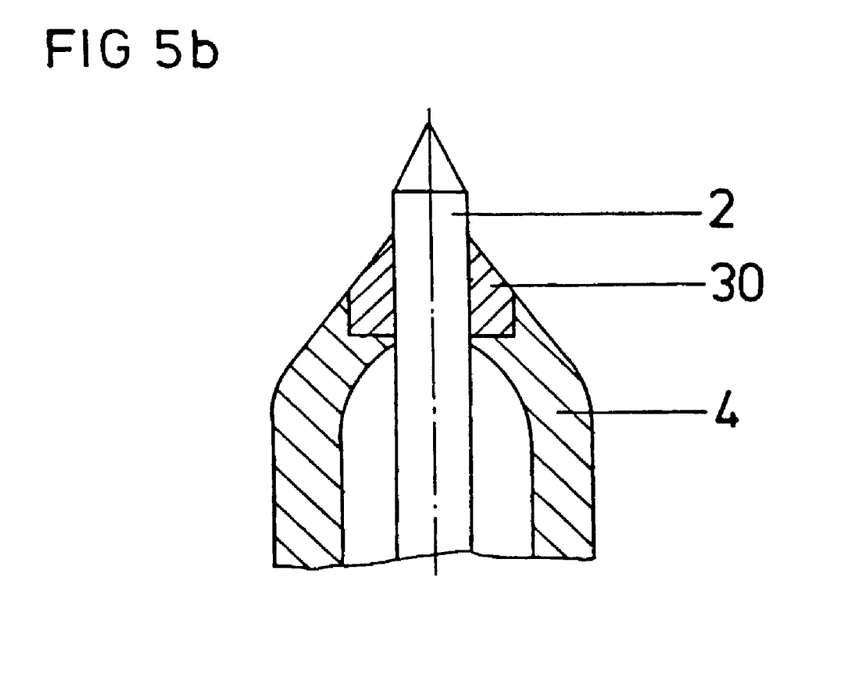
FIG. 5b shows a detailed illustration of a holding fixture for accommodating the first electrode according to a fourth embodiment, with the first electrode in the swiveled position.

FIG. 5 shows a cross-sectional representation of a measuring device according to the present invention in which the pivotable mounting of the first electrode is provided almost exclusively by sheath 4, the first electrode being introduced at its end opposite the tip into a very flat recess 26, without further holding means, thereby ensuring that this end of the first electrode is positioned in the center of the measuring device.

First electrode 2 is closely surrounded by the sheath in the region of the tip, an elastomeric gasket 30 preferably being situated between first electrode 2 and sheath 4. Gasket 30 which is in contact with first electrode 2 allows first electrode 2 to be displaced relative to gasket 30 in order to compensate for the length of the sheath when first electrode 2 is pivoted.

Figure 6A:
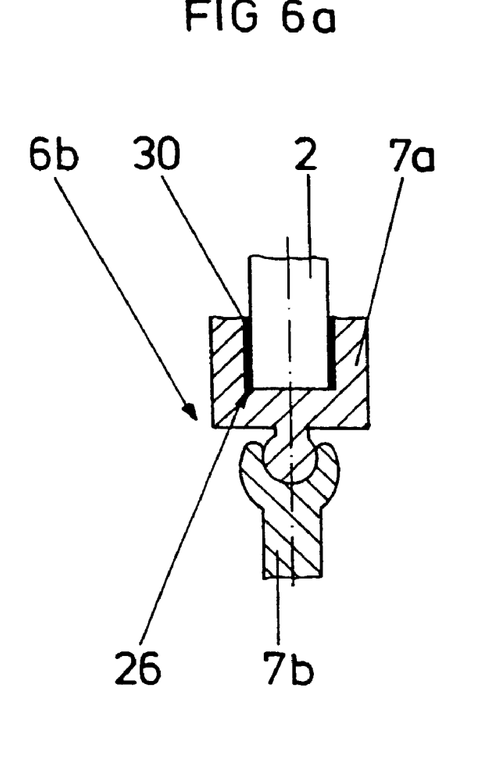
FIG. 6a shows a detailed illustration of a holding fixture for accommodating the first electrode according to a further embodiment, with the first electrode in the unswiveled position.
Figure 6B:
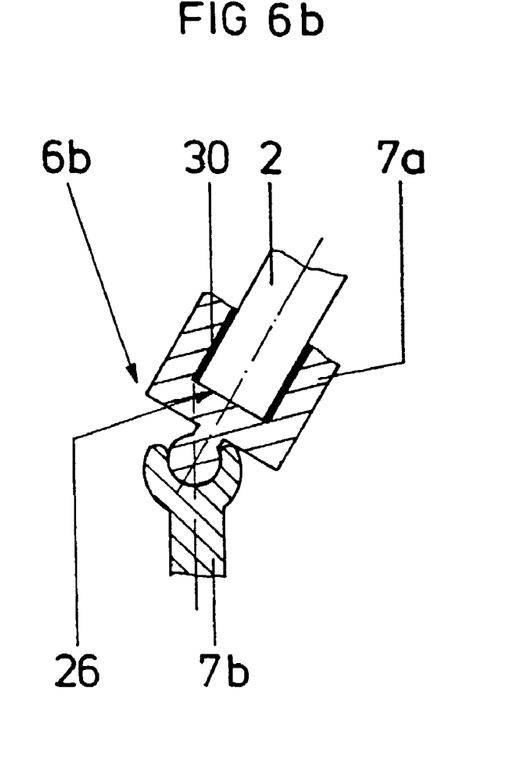
FIG. 6b shows a detailed illustration of a holding fixture for accommodating the first electrode according to a further embodiment, with the first electrode in the swiveled position.

FIG. 6 shows a further holding fixture 6b as part of a device for pivotably mounting first electrode 2. Holding fixture 6b has a ball-and-socket joint having first and second joint halves 7a, 7b, first joint half 7a having recess 26 for accommodating the one end of first electrode 2 in which the end of the first electrode is preferably glued using an adhesive 60. FIG. 6a shows the ball-and-socket joint in the rest position, and FIG. 6b shows the ball-and-socket joint in the swiveled position of first electrode 2.

Figure 7:
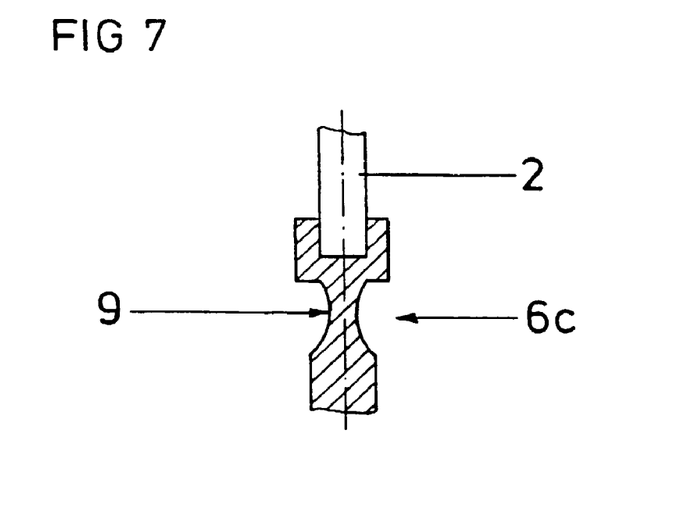
FIG. 7 shows a detailed illustration of a holding fixture for accommodating the first electrode according to a further embodiment of the present invention.

A further embodiment of a holding fixture 6c as part of a device for pivotably mounting first electrode 2 is illustrated in FIG. 7. Holding fixture 6c has a shank containing a receptacle 28 in which the first electrode is secured, preferably by using an adhesive 30. The shank has a region 9 having a smaller diameter about which the shank is able to pivot under transverse loads.

FIG. 8 shows a sectional representation of the measuring device according to the present invention in a cross-sectional side view during a measurement. The measuring device is inserted with first electrode 2 and a portion of the sheath into a material to be measured 40, being subjected to a transverse load by lateral forces F, due to the fact that the measuring device is inserted into the material to be measured at an angle and then an attempt is made to pull the measuring device out straight, for example, or due to the fact that the tip of first electrode 2 avoids a solid obstruction in material to be measured 40. Flexible sheath 4 follows the pivoting motion of probe 2, it being possible to compensate for the length at point 22 on the sheath at which probe 2 is surrounded due to the fact that the first electrode is supported by sheath 4 so that the first electrode is slightly displaceable.

Compared to the measuring devices of the related art, the measuring device according to the present invention has only one sheath, so that smaller holes remain in the material to be measured after the measurement has ended.

What is claimed is:

1. A measuring device, comprising:
a first electrode for insertion into a material to be measured;
a sheath which at least partially surrounds the first electrode, and
a holding fixture in which an axial end of said first electrode is disposed, wherein the holding fixture includes a recess which accommodates the axial end of the first electrode and includes an articulated support, coupled to the recess, which pivotably mounts the first electrode, wherein the articulated support of the holding fixture enables pivoting motion of the first electrode about an imaginary hinge point, the pivoting motion of the first electrode being independent of a flexing of the first electrode, the first electrode pivoting about the imaginary hinge point in response to the material to be measured applying a transverse load to the first electrode, and wherein said sheath has an increased diameter in a region of said articulated support.

2. The measuring device as recited in claim 1, wherein the sheath is made of a flexible material.

3. The measuring device of claim 2, wherein said flexible material is a flexible plastic.

4. The measuring device as recited in claim 1, wherein a chamber is formed between the first electrode and the sheath in which a second electrode for the measuring device is mounted.

5. The measuring device of claim 4, wherein said first and second electrodes have an electrical connection to a processing device.

6. The measuring device of claim 5, wherein said holding fixture is provided in a region at an end of said first electrode facing away from another end of said first electrode which is inserted into the material to be measured.

7. The measuring device of claim 6, wherein the recess has a base with an opening for passage of connection leads.

8. The measuring device of claim 7, wherein a diameter of said opening is smaller than a diameter of said first electrode.

9. The measuring device as recited in claim 1, wherein at least one of the first electrode and the sheath for the first electrode is made of glass.

10. The measuring device as recited in claim 1, wherein the holding fixture has an accommodating recess which forms a support for the axial end of the first electrode.

11. The measuring device as recited in claim 10, wherein lateral support is provided by arranging, between the first electrode and a side face of the recess, a ring-shaped element which surrounds the first electrode.

12. The measuring device as recited in claim 11, wherein the ring-shaped element has a sleeve-like design, and at least partially surrounds the first electrode at one end section introduced into the recess.

13. The measuring device as recited in claim 12, wherein the ring-shaped element is made of a flexible material.

14. The measuring device of claim 13, wherein the ring-shaped element is made of an elastomer.

15. The measuring device as recited in claim 10, wherein the ring-shaped element has an essentially circular cross-section.

16. The measuring device as recited in claim 15, wherein the ring-shaped element is situated in the region of the opening in the recess.

17. The measuring device of claim 16, wherein said first electrode has a limited pivoting range determined at least substantially by a design of said sheath.

18. The measuring device as recited in claim 10, wherein the recess has a truncated cone-shaped design and forms a support for the axial end of the first electrode at an end of the recess having a smallest diameter.

19. The measuring device of claim 18, wherein said diameter of said first electrode is greater than said smallest diameter.

20. The measuring device as recited in claim 1, wherein the sheath closely surrounds the first electrode at least one point.

21. The measuring device as recited in claim 1, wherein the sheath is closely surrounds the first electrode in at least one location on the sheath.

22. The measuring device as recited in claim 1, wherein the sheath is detachably placed on the first electrode.

23. The measuring device as recited in claim 1, wherein the holding fixture has a joint.

24. The use of a measuring device as recited in claim 1 for measuring the pH in foodstuffs.

25. The measuring device of claim 1, wherein said first electrode is essentially cylindrical.

26. The measuring device of claim 1, further comprising: an insertion tip on a front end of said first electrode.

27. The measuring device of claim 1, wherein said holding fixture includes a shank containing a receptacle in which said first electrode is secured.

28. The measuring device of claim 1, further comprising:
a gasket disposed between said first electrode and said sheath, said gasket contacting said first electrode to allow said first electrode to be displaced relative to said gasket to compensate for a length of said sheath when said first electrode is pivoted.

29. The measuring device of claim 1, wherein elasticity of said sheath is in accordance with a transverse load bearing capacity of said first electrode.

30. A measuring device, comprising:
a first electrode for inserting into a material to be measured;
a sheath which at least partially surrounds the first electrode; and
a pivot assembly including a recess which accommodates an axial end of the first electrode and including an articulated support, coupled to the recess, that pivotably mounts said first electrode within said sheath, wherein the articulated support of the pivot assembly enables pivoting motion of the first electrode about an imaginary hinge point, the pivoting motion of the first electrode being independent of a flexing of the first electrode, wherein the sheath is formed from a flexible material, wherein the first electrode pivots about the imaginary hinge point in response to the material to be measured applying a transverse load to the first electrode, and wherein said sheath has an increased diameter in a region of said articulated support.

31. A measuring device comprising:
means for inserting a first electrode into a material to be measured; and
means for pivotably mounting said means for inserting, wherein the means for pivotably mounting includes a recess which accommodates an axial end of the first electrode and includes an articulated support, coupled to the recess, that pivotably mounts the first electrode, wherein the articulated support enables pivoting motion of the first electrode about an imaginary hinge point, the pivoting motion of the first electrode being independent of a flexing of the first electrode, the first electrode pivoting about the imaginary hinge point in response to the material to be measured applying a transverse load to the first electrode, and wherein said means for inserting has an increased diameter in a region of said articulated support.

32. The measuring device of claim 31, further comprising:
means for electrically connecting said first electrode to a processing device for determining and displaying a measured value.

33. The measuring device of claim 31, wherein said means for pivotably mounting further comprising:
means for holding said means for inserting such that said means for inserting resists transverse loads resulting from tilting of the measuring device during at least one of insertion and withdrawal into the material to be measured such that said means for inserting pivots under transverse loads.

34. The measuring device of claim 33, wherein said means for holding further comprising:
means for accommodating an end of said means for inserting to support the means for inserting against exerted axial forces.

35. The measuring device of claim 34, further comprising:
means for supporting said means for inserting allowing a portion of said means for inserting below a predetermined position to move sideways under a transverse load such that said means for inserting pivots about an imaginary hinge point.

36. The measuring device of claim 35, wherein said means for supporting includes a ring-shaped element for supporting said means for inserting.

37. The measuring device of claim 36, wherein said ring-shaped element has a sleeve-like design.

38. The measuring device of claim 36, wherein said ring-shaped element forms an O-ring.

39. The measuring device of claim 31, wherein said means for pivotably mounting includes a sheath at least partially surrounding said means for inserting, and the measuring device further comprising:
means for compensating for a length of the sheath when the means for inserting is pivoted.

40. A measuring device, comprising:
a first electrode for insertion into a material to be measured;
a sheath which at least partially surrounds the first electrode, a holding fixture including a recess in which an axial end of said first electrode is disposed; and a pivot element in contact with said holding fixture, wherein the pivot element includes an articulated support, wherein the articulated support of the pivot element is coupled to the recess and enables pivoting motion of the first electrode about an imaginary hinge point, the pivoting motion of the first electrode being independent of a flexing of the first electrode, the first electrode being pivotably mounted using said articulated support of the pivot element, wherein the first electrode pivots about the imaginary hinge point in response to the material to be measured applying a transverse load to the first electrode, and wherein said sheath has an increased diameter in a region of said articulated support.

* * * * *